(12) United States Patent
Kimura

(10) Patent No.: US 9,869,591 B2
(45) Date of Patent: Jan. 16, 2018

(54) CARS MICROSCOPE

(71) Applicant: Hitachi, Ltd., Tokyo (JP)

(72) Inventor: Shigeharu Kimura, Tokyo (JP)

(73) Assignee: Hitachi, Ltd., Tokyo (JP)

(*) Notice: Subject to any disclaimer, the term of this patent is extended or adjusted under 35 U.S.C. 154(b) by 95 days.

(21) Appl. No.: 14/784,366

(22) PCT Filed: Aug. 22, 2013

(86) PCT No.: PCT/JP2013/072349
§ 371 (c)(1),
(2) Date: Oct. 14, 2015

(87) PCT Pub. No.: WO2015/025389
PCT Pub. Date: Feb. 26, 2015

(65) Prior Publication Data
US 2016/0076940 A1    Mar. 17, 2016

(51) Int. Cl.
*G01J 3/44* (2006.01)
*G02F 1/365* (2006.01)
*G02F 1/35* (2006.01)
*G01J 3/02* (2006.01)
(Continued)

(52) U.S. Cl.
CPC ............... *G01J 3/44* (2013.01); *G01J 3/0208* (2013.01); *G01J 3/0218* (2013.01); *G01N 21/65* (2013.01); *G02B 21/002* (2013.01); *G02B 21/0056* (2013.01); *G02F 1/353* (2013.01);
(Continued)

(58) Field of Classification Search
CPC .......... G01J 3/44; G01J 3/0208; G01J 3/0217; G02F 1/353; G02F 1/365; G02F 2001/3528; G02B 21/0056; G02B 21/002; G01N 21/65; G01N 2021/653
See application file for complete search history.

(56) References Cited

U.S. PATENT DOCUMENTS 8,120,772 B2 * 2/2012 Cicerone ............... G01J 3/02
356/301
8,792,156 B1 * 7/2014 Kieu ................... G01J 3/44
356/301
(Continued)

FOREIGN PATENT DOCUMENTS

JP    2013-171154 A    9/2013
WO   2012/125391 A1    9/2012
WO   2013/052711 A2    4/2013

OTHER PUBLICATIONS

Baumgartl, M. et al., "Alignment-free, all-spliced fiber laser source for CARS microscopy based on four-wave-mixing" Optics Express, Aug. 29, 2012, pp. 21010-21018, vol. 20, No. 19.
(Continued)

*Primary Examiner* — Dominic J Bologna
(74) *Attorney, Agent, or Firm* — Mattingly & Malur, PC

(57) ABSTRACT

To measure homodyne interference with a CARS microscope, a supercontinuum beam is used as a light source. A supercontinuum beam is generated using a nonlinear optical fiber that has normal dispersion in which the coherence between pulses is maintained. As the phases of the interference components of detected beams are the same between pulses, it is possible to integrate the interference components and thus improve the signal-noise ratio.

7 Claims, 6 Drawing Sheets

(51) Int. Cl.
*G01N 21/65* (2006.01)
*G02B 21/00* (2006.01)

(52) U.S. Cl.
CPC ....... *G02F 1/365* (2013.01); *G01N 2021/653* (2013.01); *G02F 2001/3528* (2013.01)

(56) References Cited

U.S. PATENT DOCUMENTS

| | | | | |
|---|---|---|---|---|
| 2010/0309465 | A1* | 12/2010 | Liu | G01J 3/44 356/301 |
| 2011/0128538 | A1* | 6/2011 | Cerullo | G01J 3/44 356/301 |
| 2012/0287428 | A1* | 11/2012 | Tamada | G01J 3/10 356/301 |
| 2012/0292531 | A1 | 11/2012 | Grudinin et al. | |
| 2013/0215422 | A1* | 8/2013 | Kimura | G01J 3/45 356/301 |
| 2014/0063495 | A1* | 3/2014 | Kimura | G01N 21/65 356/300 |

OTHER PUBLICATIONS

James P. R. Day et al., "Quantitative Coherent Anti-Stokes Raman Scattering (CARS) Microscopy," J. Phys. Chem. B, Apr. 28, 2011, pp. 7713-7725, vol. 115.

Conor L. Evans et al., "Coherent Anti-Stokes Raman Scattering Spectral Interferometry: Determination of the Real and Imaginary Components of Nonlinear Susceptibility $\chi(3)$ for Vibrational Microscopy," Optics Letters, Dec. 15, 2004, pp. 2923-2925, vol. 29, No. 24.

Masanari Okuno et al., "Quantitative CARS Molecular Fingerprinting of Single Living Cells with the Use of the Maximum Entropy Method," Angew. Chem. Int. Ed. 2010, pp. 6773-6777, vol. 49.

International Search Report of PCT/JP2013/072349.

* cited by examiner

CARS MICROSCOPE

TECHNICAL FIELD

The present invention relates to an optical device that requires optical resolution, and in particular, to a CARS microscope for focusing an optical beam and acquiring a response signal by changing the relative positions of the optical beam and an observation object irradiated with the optical beam.

BACKGROUND ART

Raman spectroscopic microscopes are quite effective to observe biologically-related samples. In a Raman spectroscopic microscope, an observation target is irradiated with a focused laser beam to detect Raman scattered light generated from the observation target. Raman scattered light has a shifted frequency from the frequency of the excitation light, and a Raman spectrum is measured with a spectrometer or the like. Scanning an observation target with an irradiation beam while changing their relative positions can obtain an optical spectrum at each position, and an image can be formed on the basis of such spectrum. A Raman spectrum at each observation position reflects the vibrational excited state of a molecule at the position, and thus is characteristic of the molecule. Using the characteristics of such a spectrum can know, if living cells are observed, a distribution of biomolecules in the cell tissue.

FIG. 2 shows a process by which Raman scattering occurs, using an energy level diagram. Raman scattering includes Stokes scattering and anti-Stokes scattering. FIG. 2 shows only Stokes scattering. Reference numeral 701 denotes the molecular vibrational ground state, and reference numeral 702 denotes the vibrational excited state. When a molecule is irradiated with a pump beam with a frequency top, a beam with a frequency $\omega_S$ is scattered after an intermediate state 703 is once reached. At this time, the molecule falls back to one of the levels of the vibrational excited state 702. The scattered beam with the frequency $\omega_S$ is a Stokes beam with a frequency lower than that of the pump beam. The molecular vibrational excited state has a plurality of levels, and the vibrational excited state differs depending on the types of molecules. Further, as the probability of transition from the level of the intermediate state to the level of the vibrational excited state differs from molecule to molecule, a spectrum that is unique to the molecule is formed. The Raman shift frequency $\Omega$ is represented by $\Omega = \omega_P - \omega_S$, and has a positive value in the case of Stokes scattering. In the case of an anti-Stokes beam, the initial state is the molecular vibrational excited state, and the molecular state falls back to the vibrational ground state after an intermediate level is once reached. In such a case, if the frequency of the anti-Stokes beam is represented by $\omega_{AS}$, $\omega_P < \omega_{AS}$. Thus, the frequency of the anti-Stokes Raman scattered beam is higher than that of the pump beam.

Measurement of the aforementioned Raman scattering takes a long time as the intensity of the obtained scattered light is weak. As a method that can obtain intense scattered light, there is known spectroscopy that uses nonlinear Raman scattering called CARS (Coherent Anti-Stokes Raman Scattering). Using such a method can also obtain a Raman spectrum and know the molecular vibrational state. To generate CARS, pulsed laser with high peak power is used. CARS is generated from such a pulsed laser beam due to the nonlinear effect, and the intensity of the CARS becomes orders of magnitude higher than that of Raman scattering as the peak power is higher. Accordingly, it is possible to obtain a signal with a high signal-noise ratio and significantly reduce the measurement time.

CARS is based on the third-order polarization. In order to generate CARS, a pump beam, a Stokes beam, and a probe beam are required. Typically, the pump beam is substituted for the probe beam in order to reduce the number of light sources. In that case, the induced third-order polarization is represented as follows.

$$P_{AS}^{(3)}(\omega_{AS}) = |\chi_r^{(3)}(\omega_{AS}) + \chi_{nr}^{(3)}| E_P^2(\omega_P) E^*_S(\omega_S) \quad \text{[Formula 1]}$$

Herein, $\chi_r^{(3)}(\omega_{AS})$ is a resonant term of a vibration of a molecule with the third-order electric susceptibility, and $\chi_{nr}^{(3)}$, which has no frequency dependence, is a nonresonant term. In addition, the electric fields of the pump beam and the probe beam are represented by $E_P$, and the electric field of the Stokes beam is represented by $E_S$. In Formula (1), the asterisk that appears in $E_S$ represents the complex conjugate. The intensity of a CARS beam is represented as follows.

$$I_{CARS}(\omega_{AS}) \propto |P_{AS}^{(3)}(\omega_{AS})|^2 \quad \text{[Formula 2]}$$

A mechanism by which a CARS beam is generated will be described using a molecular energy-level diagram (FIG. 3). FIG. 3 shows a process of the resonant term. As in FIG. 2, reference numeral 701 denotes the molecular vibrational ground state, and reference numeral 702 denotes the vibrational excited state. A molecule is simultaneously irradiated with a pump beam with a frequency $\omega_P$ and a Stokes beam with a frequency $\omega_S$. At this time, the molecule is excited to a vibrational excitation level 702 after an intermediate state 703 is once reached. When the molecule in the excited state is irradiated with a probe beam with a frequency $\omega_P$, the molecule falls back to the vibrational ground state while generating a CARS beam with a frequency $\omega_{AS}$ after an intermediate state 704 is once reached. The frequency of the CARS beam at this time is represented by $\omega_{AS} = 2 \cdot \omega_P - \omega_S$.

FIG. 4 shows a process related to the nonresonant term in Formula (1). This is a process in which an intermediate state 705 is once reached but the frequency of the Stokes beam is not in the vibrational excited state. The intermediate state 705 in which electrons and the like are involved is excited when a molecule is simultaneously irradiated with a pump beam with a frequency $\omega_P$ and a Stokes beam with a frequency $\omega'_S$. When the molecule is further irradiated with a probe beam with a frequency $\omega_P$, a nonresonant CARS beam with a frequency $\omega_{AS}$ is generated after an intermediate state 704 is once reached. When a broadband laser beam is used as a Stokes beam, for example, it may contain a beam with a frequency $\omega'_S$ in FIG. 4 and the like. Such resonant CARS beam and nonresonant CARS beam are coherent with each other and thus interfere with each other.

Since Raman scattering was first discovered in 1928, a spectrum of a variety of molecules has been researched, and data thereon has been accumulated. Thus, it is desirable to identify molecules with reference to such spectral data. A CARS beam is represented by Formulae (1) and (2), and $\text{Im}[\chi_r^{(3)}(\omega_{AS})]$ is a portion corresponding to the Raman scattering spectrum. This is the complex portion of the resonant term, and interferes with the nonresonant term $\chi_{nr}^{(3)}$ as described above. Thus, the shape of the spectrum obtained from CARS differs from that of the Raman scattering spectrum $\text{Im}[\chi_r^{(3)}(\omega_{AS})]$. Therefore, it would be difficult to directly analyze a CARS spectrum with reference to the Raman scattering spectrum.

Development of a method for extracting a Raman scattering spectrum from a CARS spectrum is an important challenge to be addressed, and a variety of methods has been developed (Non Patent Literature 1). For example, the maximum entropy method, which is a method for restoring a phase spectrum from an intensity spectrum, includes determining a complex portion of a resonant term through mathematical computation. Alternatively, a method that uses interference is also known (Non Patent Literature 2).

As a spectral region that is sensitive to the molecular structure, there is a Raman scattering spectral region (of from 1800 to 800 cm$^{-1}$) called a fingerprint region. For detection of a CARS beam, a spectrum in a similar region is desirably obtained. In the method introduced in Non Patent Literature 1, the spectral bandwidth of a Stokes beam for excitation is about 140 cm$^{-1}$, which cannot cover such region. Non Patent Literature 3 introduces a method that uses a photonic fiber for a light source to cover such deficiency. Specifically, the method includes irradiating a photonic fiber with ultrashort pulsed laser to generate a broadband beam called a supercontinuum beam, and using it as a Stokes beam.

CITATION LIST

Non Patent Literature

Non Patent Literature 1: J. P. R. Day, K. F. Domke, G. Rago, H. Kano, H. Hamaguchi, E. M. Vartiainen, and M. Bonn "Quantitative Coherent Anti-Stokes Raman Scattering (CARS) Microscopy," J. Phys. Chem. B, Vol. 115, 7713-7725 (2011)

Non Patent Literature 2: C. L. Evans, E. O. Potma, X. S. and Xie, "Coherent Anti-Stokes Raman Scattering Spectral Interferometry: Determination of the Real and Imaginary Components of Nonlinear Susceptibility $\chi$ (3) for Vibrational Microscopy," Opt. Lett. Vol. 29, 2923-2925 (2004)

Non Patent Literature 3: M. Okuno, H. Kano, P. Leproux, V. Couderc, J. P. R. Day, M. Bonn, and H. Hamaguchi, "Quantitative CARS Molecular Fingerprintig of Single Living Cells with the Use of the Maximum Entropy Method," Angew. Chem. Int. Ed. Vol. 49, 6773-6777 (2010)

SUMMARY OF INVENTION

Technical Problem

A method for observing living cells using a CARS beam is advantageous in that it is "noninvasive." In order to generate a CARS beam, a measurement target is simultaneously irradiated with a pump beam and a Stokes beam that are ultrashort pulsed beams. Typically, as the wavelengths of the two excitation beams used for CARS, wavelengths that are not absorbed by living cells are used. Thus, the method can be said to be "noninvasive" under low peak power conditions and thus will hardly damage cells. However, if the peak power is increased too much, a multi-photon process may occur, which in turn may influence the cells. Thus, even though the method is "noninvasive," the peak power of beams that irradiate living cells is desirably low. An object of the present invention is to improve the signal-to-noise ratio of a weak CARS signal that is generated under suppressed peak power conditions of excitation beams.

Solution to Problem

A CARS microscope for solving the above problem includes a first laser beam with a frequency $\omega_P$; a normal dispersion nonlinear optical fiber excited by the first laser beam; a second laser beam with a frequency $\omega_{ST}$ in a supercontinuum beam (hereinafter referred to as a SC beam) generated from the nonlinear optical fiber; a third laser beam as a reference beam with a frequency $\omega_{AS}=2\cdot\omega_P-\omega_{ST}$ in the SC beam generated from the nonlinear optical fiber; an optical unit configured to align the first beam and the second beam on the same axis; a mechanism for adjusting the phases of the first beam and the second beam; an objective lens configured to focus the first and second laser beams; a scanning mechanism for scanning the observation sample; an objective lens configured to detect a CARS beam generated from the observation sample; an interference optical unit configured to cause the CARS beam and the third beam to interfere with each other; spectrometers each configured to disperse the interference beam; photodetectors each configured to detect the dispersed beam; a computing unit configured to process signals from the photodetectors; and a display device configured to display an image on the basis of information of the computing unit.

As a method that can distinguish between a change in the number of molecules in a measurement region and a change in a spectrum that occurs due to a change in the molecular structure, a method that uses a broadband beam as a Stokes beam is adopted. Although the present invention uses a SC beam as a broadband beam, such SC beam has not been used as a light source for measurement of homodyne interference, which may be able to improve the signal-to-noise ratio of a CARS signal, so far. This is because, in order to obtain a broadband, coherent SC beam, which is required to generate a CARS beam and is required for homodyne measurement, an excitation light source with a pulse width of several femtoseconds would be needed, which is not very realistic. In the present invention, a highly coherent SC beam is used as a light source to improve the signal-to-noise ratio of a CARS signal.

Advantageous Effects of Invention

According to the present invention, it is possible to integrate interference beams of a CARS beam generated for each laser pulse and a reference beam on each detector, and thus improve the signal-to-noise ratio. In order to maintain the coherence for each pulse of a SC beam, which is generated without using a normal dispersion nonlinear optical fiber, it would be necessary to perform excitation using an ultrashort pulse with a pulse width on the order of 10 femtoseconds. In order to generate such an ultrashort pulsed laser beam, an expensive solid-state laser would be required at present. Therefore, CARS microscopes become expensive and the spread of CARS microscopes for purposes other than research becomes difficult. In contrast, if a normal dispersion nonlinear optical fiber is used, it becomes possible to maintain the coherence for each pulse of a laser beam with a pulse width of greater than or equal to 100 femtoseconds. In such a case, although the peak power of the laser beam needs to be higher than when optical fibers of other type dispersion are used, this can be addressed by using a fiber laser. Thus, a less expensive optical device configuration can be provided.

Other problems, configurations, and advantageous effects will become apparent from the following description of embodiments.

DESCRIPTION OF EMBODIMENTS

Hereinafter, embodiments for carrying out the present invention will be described with reference to the drawings.
[Embodiment 1]

Figure 1:
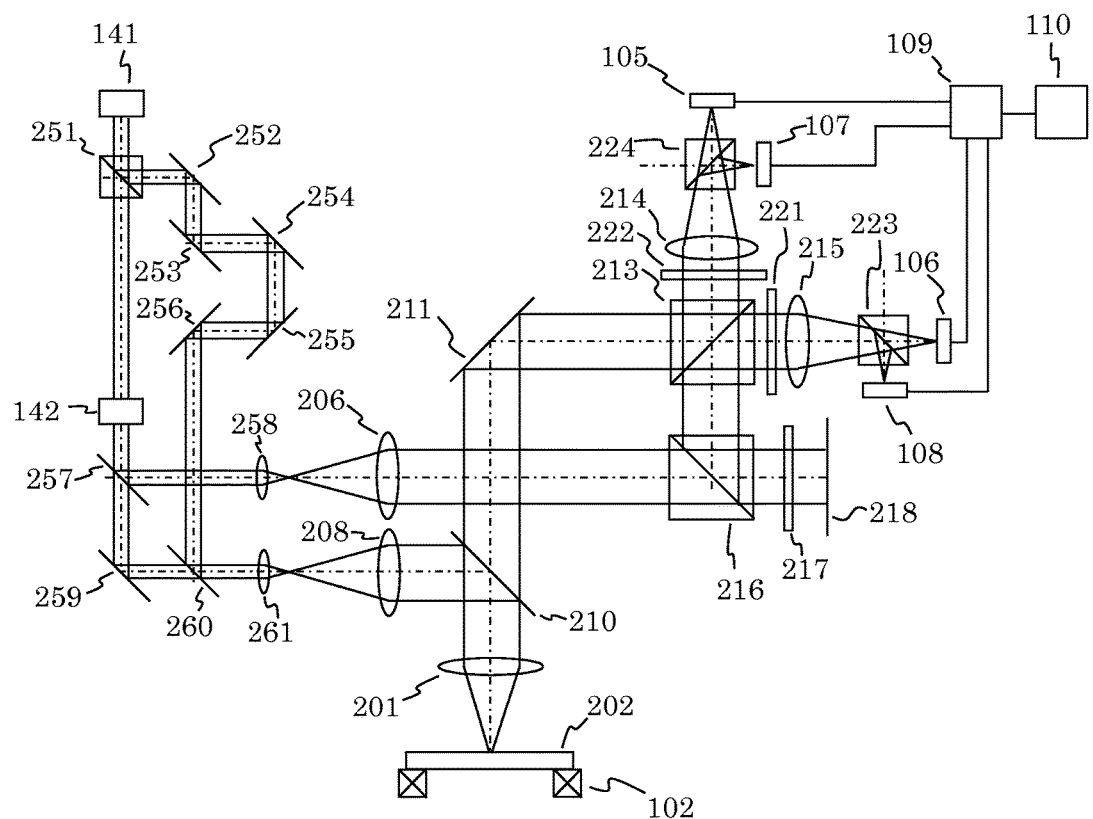
FIG. 1 shows an example of a CARS microscope in accordance with the present invention.
Figure 2:
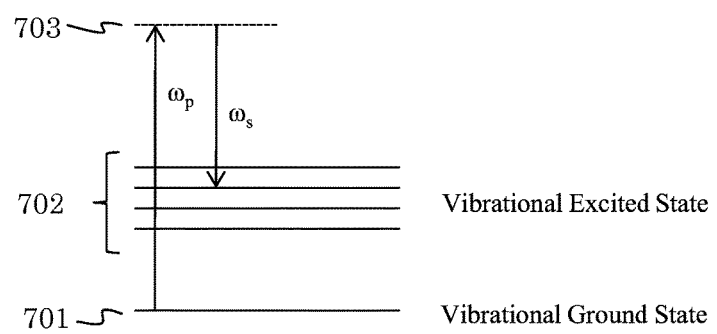
FIG. 2 is an energy level diagram of Stokes scattering of ordinary Raman scattering.
Figure 3:
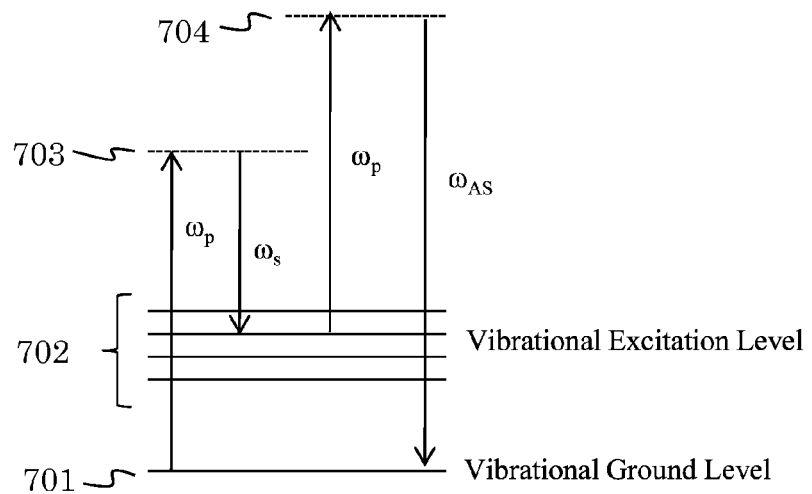
FIG. 3 is an energy level diagram of CARS.
Figure 4:
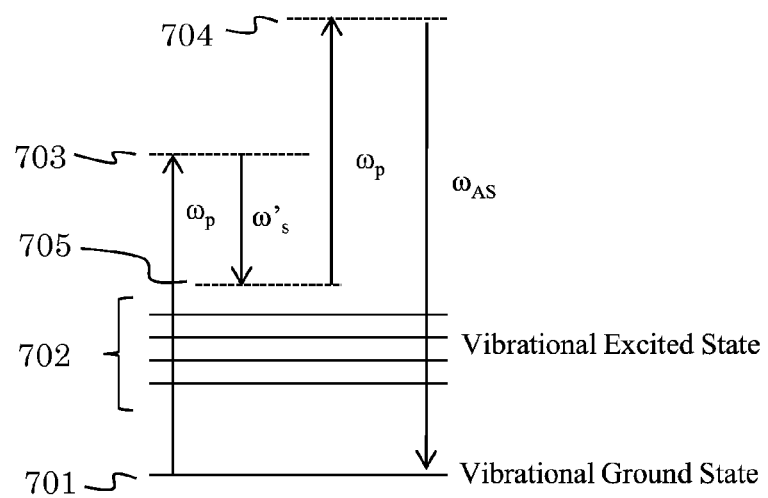
FIG. 4 is an energy level diagram illustrating an example of a nonresonant beam of CARS.
Figure 5:
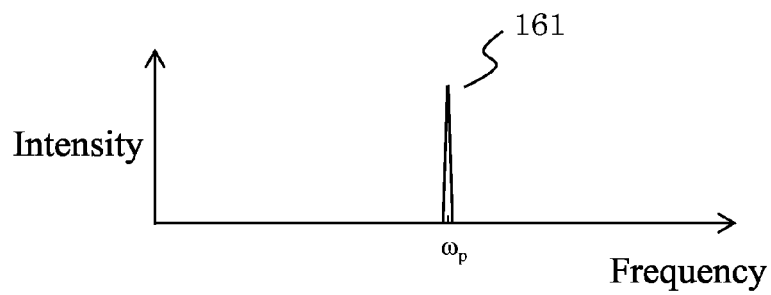
FIG. 5 shows a frequency spectrum of a pulsed laser beam.

FIG. 1 shows an example of a CARS microscope in accordance with the present invention. Reference numeral 141 denotes a pulsed laser light source with a pulse width of 200 femtoseconds, for example, and emits a laser beam 161 (e.g., first beam) with the center frequency top shown in the spectrum of FIG. 5. The polarization direction of the emitted laser beam is s-polarization, and the beam is split in two by a beam splitter 251. A beam that has passed through the beam splitter enters a nonlinear photonic crystal optical fiber 142 that exhibits normal dispersion characteristics. The incident beam is converted into a supercontinuum beam (i.e., SC beam) as shown by a spectrum 162 in FIG. 6. A SC beam has a wide frequency range including the excitation light frequency top, and the coherent properties of pulses are maintained. It is acceptable as long as the nonlinear photonic crystal optical fiber 142 has normal dispersion at least in the frequency region in which a SC beam is generated.

Figure 6:
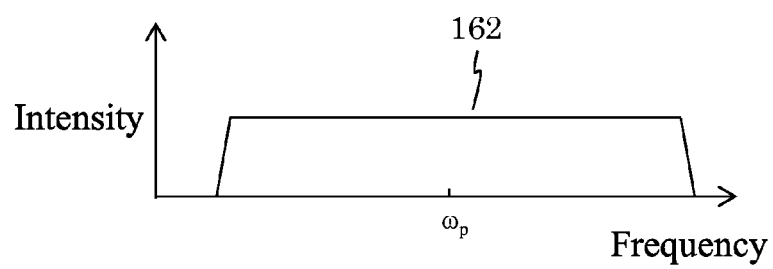
FIG. 6 shows a frequency spectrum of a supercontinuum beam.
Figure 9:
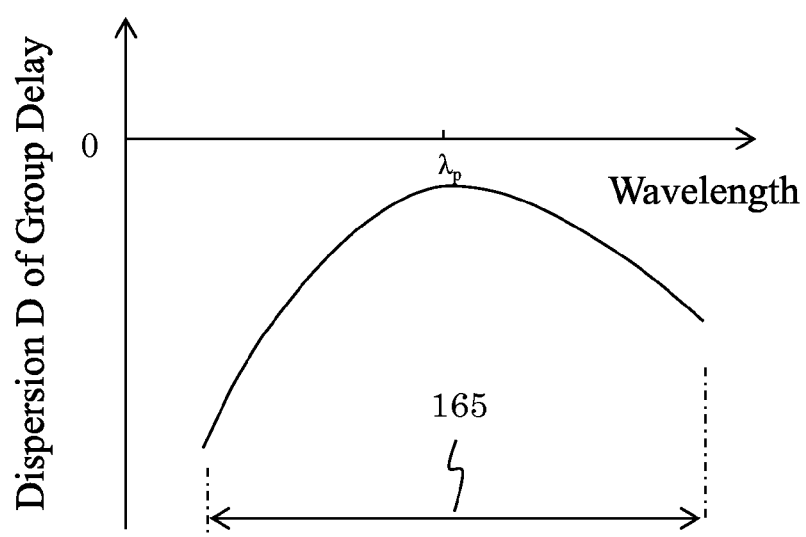
FIG. 9 shows an example of the dispersion characteristics of a normal dispersion nonlinear optical fiber.

FIG. 9 shows an example of the dispersion characteristics of the nonlinear photonic crystal optical fiber 142. The abscissa axis indicates the wavelength, and $\lambda_P$ indicates the wavelength of the first beam. The ordinate axis indicates the dispersion D of a group delay. The wavelength range shown by an arrow 165 corresponds to the frequency range in which the SC beam 162 in FIG. 6 is generated. In such a wavelength range, the photic crystal fiber has normal dispersion characteristics, and the dispersion of the group delay is in a negative region. The dispersion of the group delay becomes the maximum at the wavelength $\lambda_P$ of the first beam that is a pump beam, and D becomes smaller at wavelengths that are farther from the wavelength $\lambda_P$. Provided that the wavelength $\lambda_P$ of the first beam is 1064 nm, D is estimated to be in the range of about −10 ps/km/nm to −300 ps/km/nm.

The frequency range in which a SC beam is generated desirably reaches a maximum of ±3000 $cm^{-1}$ of the frequency top of the first beam. This is because if an organic substance in a living cell is to be observed, a stretching vibration of 2930 $cm^{-1}$ of $CH_3$ or a stretching vibration of 2850 $cm^{-1}$ of $CH_2$ may be a target to be observed, and thus that such bands should be included in the frequency range. However, as a spectral range that is effective in identifying molecules is in the range of about 800 to 1800 $cm^{-1}$ (i.e., fingerprint region), a SC beam in a narrow frequency range may be sufficient in some cases. The photonic crystal fiber may be provided with a polarization-maintaining optical fiber. In that case, the polarization direction is stabilized, and thus, the intensity and the spectral shape of a SC beam are also stabilized.

Figure 7:
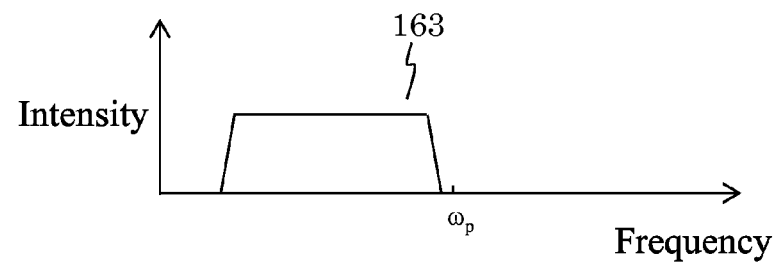
FIG. 7 shows a frequency spectrum of a low-frequency region of a supercontinuum beam used as a Stokes beam.
Figure 8:
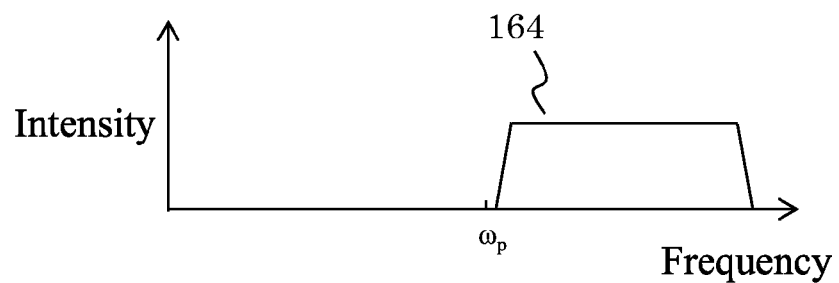
FIG. 8 shows a frequency spectrum of a low-frequency region of a supercontinuum beam used as a reference beam.

The SC beam is split in two by a dichroic mirror 257, with the frequency $\omega_P$ as the boundary. That is, a beam with a low frequency shown by a region 163 in FIG. 7 passes through the dichroic mirror, while a beam with a high frequency in a region shown by a spectrum 164 in FIG. 8 is reflected. A beam that has passed through the dichroic mirror 257 (i.e., second beam) is reflected by a mirror 259, passes through a dichroic mirror 260, and is used as a broadband Stokes beam with a frequency $\omega_{ST}$. Meanwhile, a laser beam to be used as a pump beam with the center frequency top also becomes incident on the dichroic mirror 260. Specifically, the laser beam is reflected by the beam splitter 251, and is further reflected by a mirror 252 and mirrors 253, 254, 255, and 256 for adjusting the optical path difference, and then reaches the dichroic mirror 260. The two laser beams become coaxial beams and are collimated by lenses 261 and 208. Then, the collimated beams are reflected by a dichroic mirror 210, and are focused onto an observation sample 202 by an objective lens 201. An observation object is configured to be scanned with a scanning mechanism 102. Although this embodiment adopts a method of directly scanning an observation object to avoid complexity of optics, the present invention is not limited thereto, and it is also possible to use a method in which optics for moving a focused spot is mounted. A CARS beam with a frequency $\omega_{AS}=2\cdot\omega_P-\omega_{ST}$ generated from the observation object passes through the objective lens 201 and the dichroic mirror 210, and is reflected by a reflecting mirror 211, and then enters a half beam splitter 213.

A laser beam in the high-frequency region reflected by the dichroic mirror 257 is also a SC beam, and is used as a local beam including the frequency (2·ωP−ωST), that is, a reference beam (i.e., third beam). The reference beam is collimated by lenses 258 and 206, and passes through a polarization beam splitter 216 and a Fresnel rhomb waveplate 217 having the effect of a λ/4 plate, and is then returned to the Fresnel rhomb waveplate 217 by a mirror 218. The mirror 218 is used to adjust the optical path length. A laser beam that has passed through the Fresnel rhomb waveplate 217 is a p-polarized beam, which is then reflected by the polarization beam splitter 216, and travels toward the half beam splitter 213.

It follows that beams polarized in different directions enter the half beam splitter 213 from two directions, and the beams are split in two directions, so that interference beams are emitted in two directions. A method called phase-diversity detection is used to detect $|E_{AS}(\omega)|$. A Fresnel rhomb waveplate 221 having the effect of a λ/2 plate whose optical axis is tilted by 22.5 degrees is disposed for interference beams that are emitted to the right of the half beam splitter 213 on the paper surface. Then, the interference beams are focused onto spectrometers disposed at the focus positions by a condensing lens 215. A polarization beam splitter 223 is disposed in the optical path before the spectrometers, so that the interference beams are decomposed into components in the s direction and the p direction, which are then detected by spectrometers 106 and 108, respectively. Herein, it is assumed that the observation object is a point object in the optical axis on the focal plane, and the complex amplitude of a CARS beam with a frequency ω from the observation object and the complex amplitude of the reference beam are represented by $E_{AS}(\omega)$ and $E_{LO}(\omega)$, respectively. Provided that a differential signal of the spectrometers 106 and 108 at the respective wavelengths is $I_C(\omega)$, the differential signal $I_C(\omega)$ is represented as follows.

$$I_C(\omega)=\alpha|E_{AS}(\omega)|\cdot|E_{LO}(\omega)|\cos\Phi(\omega). \quad \text{[Formula 3]}$$

Symbol $\alpha$ represents a coefficient including signal amplification, the efficiency of the spectrometers, and the like, and symbol $\Phi(\omega)$ represents the phase difference between the CARS beam from the observation object and the reference beam. A Fresnel rhomb waveplate 222 having the effect of a $\lambda/4$ plate whose optical axis is tilted by 45 degrees is inserted for interference beams that are emitted in the upward direction of the half beam splitter 213 on the paper surface. The interference beams focused by a condensing lens 214 are detected by spectrometers 105 and 107. Specifically, the interference beams are separated into s-polarized beams and p-polarized beams by a polarization beam splitter 224 disposed in the optical path, which are then detected by the respective spectrometers. Herein, provided that a differential signal of the spectrometers 105 and 107 at the respective wavelengths is $I_S(\omega)$, the differential signal $I_S(\omega)$ is represented as follows.

$$I_S(\omega)=\alpha|E_{AS}(\omega)|\cdot|E_{LO}(\omega)|\sin\Phi(\omega). \quad \text{[Formula 4]}$$

Only interference components are detected in $I_C(\omega)$ and $I_S(\omega)$. A computing unit 109 performs computation represented as follows.

$$I(\omega)=\sqrt{(I_C^2(\omega)+I_S^2(\omega))}=\alpha|E_{AS}(\omega)|\cdot|E_{LO}(\omega)| \quad \text{[Formula 5]}$$

$I(\omega)$ is proportional to the amplitude of the CARS beam from the observation object and the amplitude of the reference beam. Thus, if the wavelength dependence of $|E_{LO}(\omega)|$ is small, increasing $|E_{LO}(\omega)|$ can obtain $I(\omega)$ with amplified $|E_{AS}(\omega)|$. Typically, the spectrum of a SC beam is not flat. Thus, in order to obtain a more accurate spectrum $I(\omega)$, it is necessary to perform correction using the amplitude spectrum of the SC beam.

Next, the complex components of the resonant term of the CARS beam are extracted to extract the Raman scattering spectrum. $\Phi(\omega)$ that is the phase difference between the local beam and the CARS signal beam is represented by $\Phi(\omega)=\omega\tau+\theta_S(\omega)+\theta_{inst}(\omega)$. Symbol $\omega\tau$ represents the optical path difference between the two beams, $\theta_S(\omega)$ represents the phase difference due to a resonant beam, and $\theta_{inst}(\omega)$ represents the phase difference derived from the device. Herein, it is assumed that the local beam has no frequency dependence. $\tan\Phi(\omega)$ is determined from Formulae (3) and (4), and $\Phi(\omega)$ can also be determined. First, as an observation sample, a sample that generates only a nonresonant CARS beam is measured to determine $\omega\tau+\theta_{inst}(\omega)$ Next, an observation sample that generates resonant CARS is measured. Accordingly, $\theta_S(\omega)$ can be determined. Thus, the complex number portion of the resonant components can be determined as $I(\omega)\sin\theta_S(\omega)$. Accordingly, a portion corresponding to the Raman scattering spectrum can be obtained. Detectors such as CCDs may be used for detection of beams with the spectrometers. The display device 110 displays the scanned position and the display position of the observation object 202 in association with each other. Displaying the complex components of a resonant beam at a frequency position that is characteristic of a molecular vibration can know a distribution of molecules.

In this embodiment, a number of pulses are integrated. If the coherence between pulses is lost, the phase of $\Phi(\omega)$ in $I_C(\omega)=\alpha|E_{AS}(\omega)|\cdot|E_{LO}(\omega)|\cos\Phi(\omega)$ or $I_S(\omega)=\alpha|E_{AS}(\omega)||E_{LO}(\omega)|\sin\Phi(\omega)$ becomes random, so that the value of $I_C(\omega)$ or $I_S(\omega)$ obtained by integrating a number of pulses becomes zero. However, as a SC beam generated from a normal dispersion nonlinear optical fiber is used in this embodiment, the coherence between pulses is maintained. Thus, there is no possibility that $I_C(\omega)$ or $I_S(\omega)$ may become zero, which would otherwise occur if there is no coherence between pulses.

Figure 10:
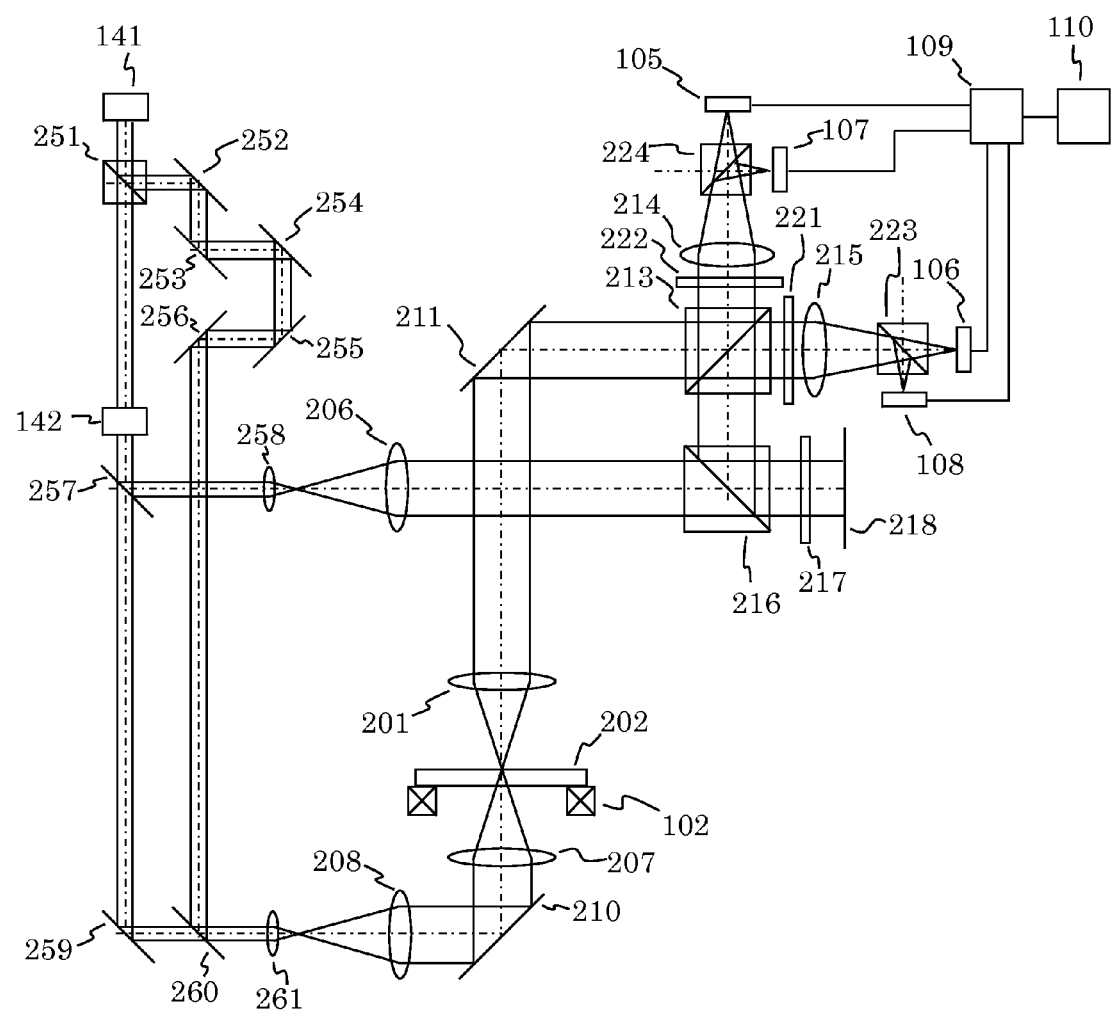
FIG. 10 shows an example of a CARS microscope in accordance with the present invention.

FIG. 10 shows an embodiment of a transmission-type CARS microscope in accordance with the present invention. The direction in which a CARS beam is strongly emitted differs depending on the shape and the size of an observation object. Typically, back scattering of a CARS beam becomes weaker as an observation object, which contains a molecule that generates a CARS beam, is larger. To the contrary, forward scattering exhibits the opposite dependence. The example shown in FIG. 10 has a configuration for detecting a CARS beam when the forward scattering is strong. The configuration in FIG. 10 differs from that in FIG. 1 in that an observation sample is irradiated with a pump beam and a Stokes beam from an opposite direction of the observation sample. That is, a Stokes beam (i.e., second beam) that has passed through the dichroic mirror 257 and a pump beam (i.e., first beam) reflected by the mirror 256 are made coaxial beams by the mirror 259 and the dichroic mirror 260, and are then collimated by the lenses 261 and 208. The collimated coaxial laser beams are reflected by the dichroic mirror 210, and are then focused onto the observation sample 202 by an objective lens 207. A CARS beam generated in the forward direction from the observation sample passes through the objective lens 201, so that interference measurement similar to that in the embodiment shown in FIG. 1 is performed.

Although the embodiment shown in FIG. 1 and the embodiment shown in FIG. 10 use different optical units, it is also possible to use a single optical unit by switching the optical path.

In the aforementioned embodiment, a method of causing linearly polarized beams, which are orthogonal to each other, to interfere with each other is adopted to perform phase diversity detection. As an alternative method, it is also possible to use a method of converting a CARS beam from an observation object and a reference beam into a right-handed circularly polarized beam and a left-handed circularly polarized beam that are orthogonal to each other, and causing the beams to interfere with each other. For example, a CARS beam is converted into a right-handed circularly polarized beam, and a reference beam is converted into a left-handed circularly polarized beam. When the optical axes of analyzers for detecting the interference beams are set to 0, 45, 90, and 135 degrees, respectively, it is possible to obtain beams with phase differences of 0, 90, 180, and 270 degrees. Combining such signals can obtain a signal represented by Formula (5) and obtain effects that are similar to those in the aforementioned embodiment.

[Embodiment 2]

Figure 11:
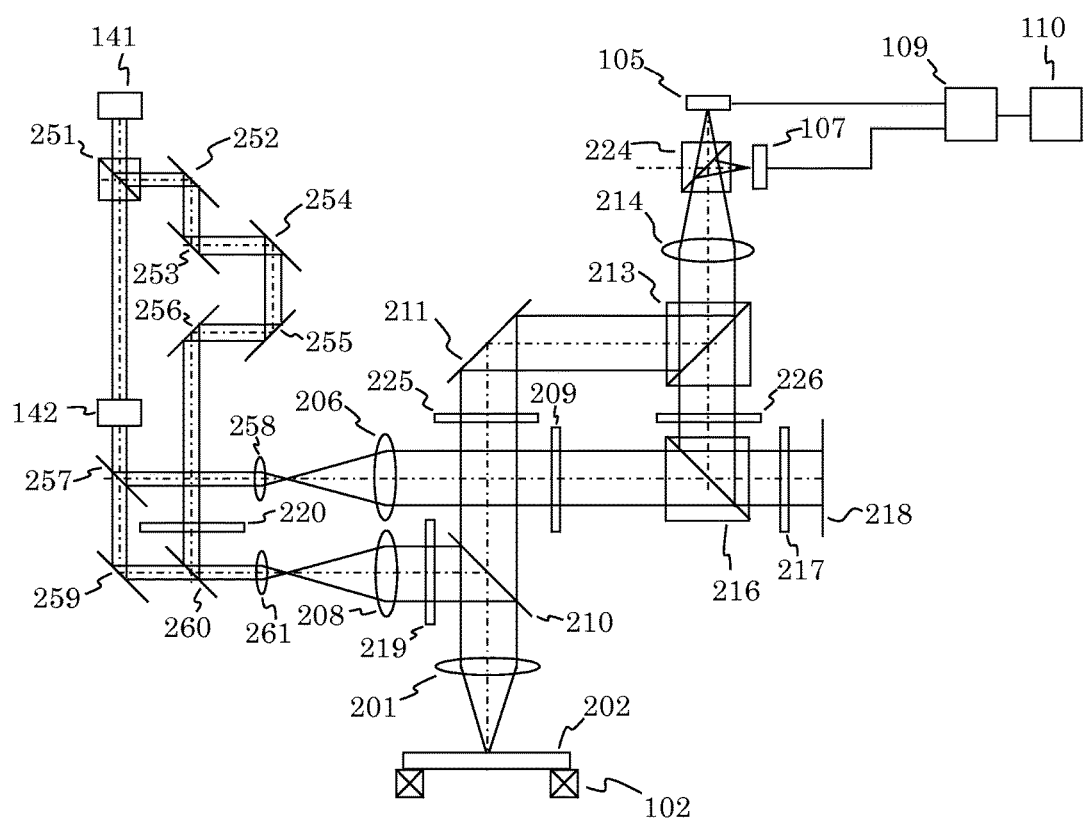
FIG. 11 shows an example of a CARS microscope in accordance with the present invention.

FIG. 11 shows another embodiment of a CARS microscope in accordance with the present invention. In the embodiment shown in FIG. 11, the number of beams that are detected in the embodiment shown in FIG. 1 is set to two in order to simplify the configuration. A pump beam (i.e., first beam) and a Stokes beam (i.e., second beam) that have been made coaxial beams by the dichroic mirror 260 are collimated, pass through an optical shutter 219, and are focused onto the observation sample 202. A CARS beam with a frequency $\omega_{AS}=2\cdot\omega_P-\omega_{ST}$ generated from the observation sample is converted into a circularly polarized beam by a Fresnel rhomb waveplate 225, and is then caused to enter the half beam splitter 213 by the mirror 211. A laser beam (i.e., third beam) in the high-frequency region reflected by the dichroic mirror 257 is collimated by the lenses 258 and 206, and is used as a reference beam including the frequency $(2\cdot\omega_P-\omega_{ST})$. The reference beam passes through an optical shutter 209 and the polarization beam splitter 216. After that, the beam is converted into a circularly polarized beam by the Fresnel rhomb waveplate 217, and is then reflected by the mirror 218 for adjusting the optical path length. The reflected reference beam becomes an opposite-handed circularly polarized beam, and is converted into a p-polarized beam by the Fresnel rhomb waveplate 217. The polarization direction of the reference beam reflected by the polarization beam splitter 216 is tilted by 45 degrees by a Fresnel rhomb waveplate 226 having the effect of a λ/2 plate whose optical axis is tilted by 22.5 degrees. The reference beam enters the beam splitter 213, and then interferes with the CARS beam from the observation sample that has entered from the left side of the beam splitter 213. The overlaid beams travel toward the condensing lens 214, and the focused interference beams are split in two by the polarization beam splitter 224, and then are focused onto the spectrometers 105 and 107.

When the optical shutters 219 and 209 are open, a signal represented by the following formula is output from the spectrometer 105, $$S_C(\omega)=|E_{LO}|^2+|E_{AS}(\omega)|^2+2|E_{LO}E_{AS}(\omega)|\cos\Phi(\omega), \quad \text{[Formula 6]}$$

and a signal represented by the following formula is output from the spectrometer 107.

$$S_S(\omega)=|E_{LO}|^2+|E_{AS}(\omega)|^2+2|E_{LO}E_{AS}(\omega)|\sin\Phi(\omega). \quad \text{[Formula 7]}$$

$|E_{LO}|^2$ and $|E_{AS}(\omega)|^2$ in Formula (6) and Formula (7) can be determined by shutting off one of them. When the optical shutter 219 is closed and the optical shutter 209 is opened, $|E_{LO}(\omega)|^2$ is output to the spectrometers 105 and 107. To the contrary, when the optical shutter 219 is opened and the optical shutter 209 is closed, $|E_{AS}(\omega)|^2$ is output to the spectrometers. The computing unit 109 computes $|E_{LO}(\omega)E_{AS}(\omega)|$ from the outputs.

Further spectral correction can be performed by measuring the Stokes beam (i.e., second beam). Though not shown, a plane mirror is inserted immediately before the objective lens 201, and an optical spectrum is measured by the spectrometers 105 and 107 with the optical shutter 219 open and the optical shutter 209 closed. The optical spectrum includes the optical spectrum of the Stokes beam $E_S(\omega)$. Thus, the influence of the spectral distribution of the Stokes beam can be corrected by taking into Formula (1) into consideration.

Using the results, a phase difference generated by the resonant beam is computed with the aforementioned method that uses interference, so that $[|E_{LO}(\omega)E_{AS}(\omega)|\sin\theta_S(\omega)]$ that is the complex component of the resonant term is extracted to obtain a result equivalent to that of Raman spectroscopy.

In this embodiment, a bandpass filter 220 is inserted in the optical path of a pump beam that is the first beam reflected by the beam splitter 251. As a laser beam emitted from the pulsed light source 141, a laser beam with a narrow pulse width is used to maintain the coherence between pulses. Therefore, the spectral bandwidth of the first beam is wide. However, if the first beam is used as it is to generate a CARS beam, a desired spectral resolution may not be obtained in some cases. To address this, a bandpass filter for narrowing the spectral bandwidth was inserted.

The present invention is not limited to the aforementioned embodiments, and includes a variety of variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add, remove, or substitute a structure of another embodiment.

INDUSTRIAL APPLICABILITY

According to the present invention, it is possible to acquire a high-resolution image using a CARS beam, and provide a noninvasive optical device for measuring a distribution of biomolecules or a change in the distribution.

REFERENCE SIGNS LIST

102 Scanning mechanism
105, 106, 107, 108 Spectrometer
109 Computing unit
110 Display device
141 Pulsed laser light source
142 Normal dispersion nonlinear photonic crystal fiber
201 Objective lens
202 Observation object
207 Objective lens
209 Optical shutter
210 Dichroic mirror
213 Beam splitter
214 Condensing lens
216 Polarization beam splitter
217 Fresnel rhomb waveplate
218 Mirror
220 Bandpass filter
221, 222 Fresnel rhomb waveplate
223, 224 Polarization beam splitter
225, 226 Fresnel rhomb waveplate

The invention claimed is:

1. A coherent anti-Stokes Raman scattering (CARS) microscope comprising:
    a pulsed laser light source configured to generate a first beam with a frequency ωP;
    a normal dispersion nonlinear optical fiber configured to receive the first beam and generate a supercontinuum beam;
    an optical element configured to select, from the supercontinuum beam, a second beam with a frequency $\omega_{ST}$ that is lower than the frequency of the first beam, and to select, from the supercontinuum beam, a third beam as a reference beam with a frequency $\omega_{AS}=2\omega_P-\omega_{ST}$;
    a mechanism including one or more mirrors configured to adjust phases of the first beam and the second beam;
    an optical unit configured to align the first beam and the second beam on a same axis;
    an objective lens configured to focus the first beam and the second beam that are coaxial beams onto an observation sample;
    a stage configured to move to scan the observation sample with the coaxial beams;
    an interference optical unit configured to cause a CARS beam generated from the observation sample and the third beam to interfere with each other;
    a plurality of beam splitters that are each configured to decompose a respective interference beam obtained from the interference optical unit;

a plurality of spectrometers each configured to detect a respective beam decomposed by one of the beam splitters;

a computing unit configured to process signals from the spectrometers; and a display device configured to display an image based on the signals processed by the computing unit.

2. The CARS microscope according to claim 1, wherein: the nonlinear optical fiber has a normal dispersion at least in a frequency region in which the supercontinuum beam is generated.

3. The CARS microscope according to claim 1, wherein: each respective interference beam is split in at least two beams, a phase difference between the beams split from the interference beam is an integral multiple of 90 degrees, and at least one phase difference is 90 degrees.

4. The CARS microscope according to claim 1, wherein the nonlinear optical fiber has a polarization-maintaining optical fiber.

5. The CARS microscope according to claim 1, wherein the supercontinuum beam has a bandwidth of approximately 3000 $cm^{-1}$ in a high-frequency direction and a low-frequency direction about the frequency $\omega_P$ of the first beam as a center.

6. The CARS microscope according to claim 1, wherein an interference beam spectrum is corrected by the computing unit using the signals from the spectrometers which correspond to the second beam.

7. The CARS microscope according to claim 1, further comprising:

an optical filter configured to narrow a spectral bandwidth of the first beam.

\* \* \* \* \*